United States Patent [19]

Kuroda et al.

[11] Patent Number: 5,250,485

[45] Date of Patent: Oct. 5, 1993

[54] PROCESS FOR PREPARING CATALYSTS USED FOR PRODUCTION OF METHACROLEIN AND METHACRYLIC ACID

[75] Inventors: Toru Kuroda; Motomu Oh-Kita, both of Otake, Japan

[73] Assignee: Mitsubishi Rayon Co., Ltd., Tokyo, Japan

[21] Appl. No.: 910,585

[22] Filed: Jul. 8, 1992

[30] Foreign Application Priority Data

Jul. 17, 1991 [JP] Japan .................... 3-176997

[51] Int. Cl.$^5$ .................... B01J 31/00
[52] U.S. Cl. .................... 502/159; 502/205; 502/212; 502/215; 502/220; 502/241; 502/242; 502/304; 502/306; 502/307; 502/308; 502/311
[58] Field of Search ........... 502/159, 205, 212, 215, 502/220, 241, 242, 304, 306, 307, 308, 311

[56] References Cited

U.S. PATENT DOCUMENTS

| | | |
|---|---|---|
| 4,032,433 | 6/1977 | Petri et al. |
| 4,168,246 | 9/1979 | Li .................... 502/212 |
| 4,405,498 | 9/1983 | Ebner .................... 502/205 |
| 4,564,607 | 1/1986 | Yoneda et al. .................... 502/209 |
| 4,954,650 | 9/1990 | Abe et al. .................... 502/2 |
| 4,966,877 | 10/1990 | Langerbeins et al. .................... 502/209 |

FOREIGN PATENT DOCUMENTS

| | | |
|---|---|---|
| 304867 | 3/1989 | European Pat. Off. |
| 456837 | 11/1991 | European Pat. Off. |
| 2543020 | 9/1984 | France |

*Primary Examiner*—Patrick P. Garvin
*Assistant Examiner*—E. D. Irzinski
*Attorney, Agent, or Firm*—Armstrong, Westerman, Hattori, McLeland & Naughton

[57] ABSTRACT

A process for preparing a catalyst used for production of methacrolein and methacrylic acid by vapor phase oxidation of isobutylene or tertiary butanol includes adding an organic high-molecular weight compound having an average particle size of 0.01 μm to 10 μm, especially polymethyl methacrylate and/or polystyrene, to a MoBiFeCoNi-based catalyst, then molding the mixture and heat treating the molded product.

1 Claim, No Drawings

PROCESS FOR PREPARING CATALYSTS USED FOR PRODUCTION OF METHACROLEIN AND METHACRYLIC ACID

BACKGROUND OF THE INVENTION

1. Field of the Invention

The present invention relates to a process for preparing catalysts used in production of methacrolein and methacrylic acid by vapor phase catalytic oxidation of isobutylene or tertiary butanol.

2. Related Art

Hitherto, many proposals have been made on process for production of methacrolein and methacrylic acid by vapor phase catalytic oxidation of isobutylene or tertiary butanol and on catalysts used therefor. Some of them use various compounds in preparation of catalysts for the purpose of control of pores as reported, for example, in Japanese Patent Kokai No. 57-119837. However, these processes have the defects such as insufficient results of reaction and reduction of catalyst activity with time and further improvement has been desired for use as industrial catalysts.

SUMMARY OF THE INVENTION

The object of the present invention is to provide a novel process for preparing catalysts used for advantageous production of methacrolein and methacrylic acid from isobutylene or tertiary butanol.

The inventors have conducted intensive research for improving conventional processes for preparation of the catalysts and as a result, have found a novel process for preparing catalysts according to which methacrolein and methacrylic acid are obtained in higher yields than when catalysts prepared by conventional processes are used.

The present invention relates to a process for preparing catalysts used for production of methacrolein and methacrylic acid by vapor phase catalytic oxidation of isobutylene or tertiary butanol with molecular oxygen which comprises adding an organic high-molecular weight compound having an average particle size of 0.01 μm to 10 μm to a catalyst component having the composition represented by the formula:

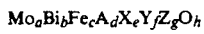

$Mo_aBi_bFe_cA_dX_eY_fZ_gO_h$ (wherein Mo, Bi, Fe and O denote molybdenum, bismuth, iron and oxygen, respectively, A denotes at least one element selected from the group consisting of nickel and cobalt, X denotes at least one element selected from the group consisting of potassium, rubidium, cesium and thallium, Y denotes at least one element selected from the group consisting of magnesium, zinc, manganese, lead, tin and chromium, Z denotes at least one element selected from the group consisting of phophorus boron, antimony, silicon, sulfur, tellurium, tungsten and cerium, a, b, c, d, e, f and g denote atomic ratios of respective elements, when a is 12, b is 0.01-3, c is 0.5-4, d is 1-12, e is 0.01-2, f is 0-5 and g is 0-20, and h is the number of oxygen atom necessary to satisfy valences of the above respective components to obtain a mixture, molding the resulting mixture to obtain a molded product and heat treating the molded product.

DETAILED DESCRIPTION OF PREFERRED EMBODIMENTS

In the present invention, it is important that at the time of the molding of the catalyst, an organic high-molecular weight compound having an average particle size in a specific range of 0.01 μm to 10 μm has been previously added to the catalyst components. When the average particle size of the organic high-molecular weight compound is less than 0.01 μm, there are caused problems in handling, for example, secondary aggregation of particles of the organic high-molecular weight compound used occurs, or dusts tends to be raised during handling of the organic high-molecular weight compound. When it is more than 10 μm, the proportion of pores preferable for the reaction in the catalyst obtained by the heat treatment after the molding is reduced, resulting in reduction of catalyst performance.

Although the effect of the addition of the organic high-molecular weight compound with the above specified average particle size on the improvement of the catalyst performance is not exactly clear, it can be speculated from the increase of pores with a diameter of approximately 100-1000 Å in the catalyst by the heat treatment (300°-650° C.) carried out after the molding into the catalyst that a pore structure ideal for the oxidation reaction which produces methacrolein and methacrylic acid from isobutylene or tertiary butanol is formed in the catalyst by the addition of the organic high-molecular weight compound.

The particle size of the organic high-molecular weight compound was measured by a scanning electron microscope, and the diameter of pores in the catalyst was measured by a mercury penetrating method.

In the present invention, although the organic high-molecular weight compound incorporated into the catalyst is not critical so long as it has an average particle size in the above range, those which are easily removable by decomposition by heating or burning, for example, polymers of methyl, ethyl, propyl or isobutyl esters of (meth)acrylic acid, and polystyrenes are preferred. Polymethyl methacrylate and polystyrene are especially preferred because they are decomposed into monomers at a relatively low temperature to vaporize and evaporate. These compounds may be used alone or as a mixture of two or more thereof.

The addition amount of the organic high-molecular weight compound is suitably 0.1 to 30% by weight based on the weight of the catalyst. When the amount is too small, the addition has no effect, and when the amount is too large, the mechanical strength of the catalyst after the heat treatment is lowered. Therefore, such inadequate and excessive amounts are not desirable.

The process for producing the catalyst having the composition used in the present invention is not critical. Various heretofore well-known methods such as evaporation-to-dryness method, precipitation method and oxide-mixing method can be used as far as extremely uneven distribution of the constituents occurs. To the thus obtained powdery catalyst component is added the organic high-molecular weight compound in wet or dry state and the resulting mixture can be molded into catalyst of a desired shape by supporting the mixture on a carrier or tabletting the mixture. However, an especially preferred result is obtained when the catalyst component is calcined at about 300° C. to decompose nitrates and others and then the organic high-molecular weight compound is added thereto. The thus molded catalyst is subject to heat treatment at 300°-650° C., preferably 350°-600° C. and the organic high-molecular weight compound added is thus removed.

As starting materials for the catalyst component having a composition represented by the above generated formula

$Mo_aBi_bFe_cA_dX_eY_fZ_gO_h$, there may be used oxides, nitrates, carbonates, ammonium salts, halides or the like of respective elements in combination. For example, ammonium paramolybdate, molybdenum trioxide, molybdenum chloride or the like can be used as a starting material for molybdenum.

The catalyst used in the process of the present invention may be free from carriers, but it may be supported on inert carriers such as silica, alumina, silica-alumina, magnesia, titania and silicon carbide or diluted therewith.

The catalyst obtained in the present invention is used for vapor phase catalytic oxidation of iso-butylene or tertiary butanol with molecular oxygen. Molar ratio of isobutylene or tertiary butanol and oxygen in this case is 1:0.5–3. The raw materials are preferably diluted with an inert gas. Economically, air is used as oxygen source, but if necessary, air enriched with pure oxygen may also be used. Reaction pressure may be from atmospheric pressure to several atm. Reaction temperature is preferably 250°-450° C. The reaction can be carried out either in a fixed bed or a fluidized bed.

Examples

The process for preparation of catalyst according to the present invention and reaction carried out using it will be specifically explained in the following examples.

In the examples and the comparative examples, conversion of isobutylene or tertiary butanol, selectivity of methacrolein and methacrylic acid produced and per-pass yield of (methacrolein + methacrylic acid) are defined as follows.

Conversion of isobutylene or tertiary butanol (%) =

$$\frac{\text{Mol of reacted isobutylene or tertiary butanol}}{\text{Mol of fed isobutylene or tertiary butanol}} \times 100$$

Selectivity of methacrolein (%) =

$$\frac{\text{Mol of produced methacrolein}}{\text{Mol of reacted isobutylene or tertiary butanol}} \times 100$$

Selectivity of methacrylic acid (%) =

$$\frac{\text{Mol of reacted methacrylic acid}}{\text{Mol or reacted isobutylene or tertiary butanol}} \times 100$$

Per-pass yield of (methacrolein + methacrylic acid) (%) =

$$\frac{\text{Mol of produced (methacrolein + methacrylic acid)}}{\text{Mol of fed isobutylene or tertiary butanol}} \times 100$$

In the following examples and comparative examples, part is by weight and analysis was carried out by gas chromatography.

EXAMPLE 1

To 1000 parts of water were added 500 parts of ammonium paramolybdate, 18.5 parts of ammonium paratungstate, 14.3 parts of potassium nitrate and 496.3 parts of 20% silica sol, followed by stirring under heating (solution A). Separately, 250 parts of 60% nitric acid was added to 850 parts of water and the mixture was homogenized and 57.2 parts of bismuth nitrate was dissolved therein. Then, to the solution were added 228.8 parts of ferric nitrate, 4.7 parts of chromium nitrate, 480.7 parts of cobalt nitrate and 70.2 parts of zinc nitrate successesively in this order and were dissolved therein (solution B). Solution B was added to solution A to prepare a slurry and 27.5 parts of antimony trioxide was added to the slurry, followed by stirring under heating to evaporate most of water.

The resulting cake was dried at 120° C. and then calcined at 300° C. for 1 hour in an air atmosphere. The resulting solid was made powdery and to 100 parts of this powder product was added 3 parts of polymethyl methacrylate (hereinafter referred to as "PMMA") having an average particle size of 0.15 μm and these were mixed. Then, the mixture was pressure molded and heat treated at 500° C. for 5 hours in an air atmosphere. This was used as a catalyst.

Composition of the elements other than oxygen (same hereinafter) of the resulting catalyst was as follows.

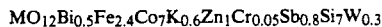
$MO_{12}Bi_{0.5}Fe_{2.4}Co_7K_{0.6}Zn_1Cr_{0.05}Sb_{0.8}Si_7W_{0.3}$

This catalyst was packed in a reaction tube and a mixed gas consisting of 5% of isobutylene, 12% of oxygen, 10% of steam and 73% of nitrogen (by volume) was passed therethrough at a reaction temperature of 360° C. for a contacting time of 3.6 seconds. The product was collected and analyzed by gas chromatography to find that conversion of isobutylene was 96.7%, selectivity of methacrolein was 87.7%, selectivity of methacrylic acid was 4.5% and per-pass yield of (methacrolein + methacrylic acid) was 89.2%.

COMPARATIVE EXAMPLE 1

A comparative catalyst having the same composition as of Example 1 was prepared in the same manner as in Example 1 except that PMMA was not added at the pressure molding. Reaction was carried out using this catalyst under the same conditions as in Example 1. The analysis revealed that conversion of isobutylene was 96.5%, selectivity of methacrolein was 87.3%, selectivity of methacrylic acid was 3.8% and per-pass yield of (methacrolein + methacrylic acid) was 87.9%.

COMPARATIVE EXAMPLE 2

A comparative catalyst having the same composition as of Example 1 was prepared in the same manner as in Example 1 except that PMMA added at the time of molding had an average particle size of 20 μm. Reaction was carried out using this catalyst under the same conditions as in Example 1. The analysis revealed that conversion of isobutylene was 96.3%, selectivity of methacrolein was 87.0%, selectivity of methacrylic acid was 3.5% and per-pass yield of (methacrolein + methacrylic acid) was 87.2%.

EXAMPLES 2-9

The catalysts as shown in Table 1 were prepared in the same manner as in Example 1 and reactions were carried out under the same conditions as in Example 1 except for the reaction temperature to obtain the results as shown in Table 1.

COMPARATIVE EXAMPLES 3-10

The comparative catalysts as shown in Table 1 were prepared in the same manners as in Examples 2-9 except that the organic high-molecular weight compound was not added at the time of pressure molding and reactions were carried out under the same conditions as in Examples 2-9 to obtain the results as shown in Table 1.

COMPARATIVE EXAMPLES 11-18

The comparative catalysts as shown in Table 1 were prepared in the same manners as in Examples 2-9 except that the organic high-molecular weight compound added at the time of pressure molding had an average particle size of larger than 10 μm and reactions were carried out under the same conditions as in Examples 2-9 to obtain the results as shown in Table 1.

EXAMPLE 10

Reaction was carried out using the catalyst of Example 1 under the same conditions as in Example 1 except that tertiary butanol was used as the starting material. The analysis revealed that conversion of tertiary butanol was 100%, selectivity of methacrolein was 86.9%, selectivity of methacrylic acid was 3.7% and per-pass yield of (methacrolein + methacrylic acid) was 90.6%.

COMPARATIVE EXAMPLE 19

Reaction was carried out using the catalyst of Comparative Example 1 under the same conditions as in Example 10. The analysis revealed that conversion of tertiary butanol was 100%, selectivity of methacrolein was 85.9%, selectivity of methacrylic acid was 3.3% and per-pass yield of (methacrolein + methacrylic acid) was 89.2%.

COMPARATIVE EXAMPLE 20

Reaction was carried out using the catalyst of Comparative Example 2 under the same conditions as in Example 10. The analysis revealed that conversion of tertiary butanol was 100%, selectivity of methacrolein was 85.7%, selectivity of methacrylic acid was 3.0% and per-pass yield of (methacrolein + methacrylic acid) was 88.7%.

TABLE 1

| | Composition of catalyst | Organic high-molecular weight compound [Average particle size/(μm)/addition amount (% by weight)] |
|---|---|---|
| Example 2 | $Mo_{12}Bi_{0.5}Fe_2Ni_7Cs_{0.4}Mg_1Sb_1W_{0.3}$ | PMMA [0.25/5] |
| Comparative Example 3 | " | No addition |
| Comparative Example 11 | " | PMMA [50/5] |
| Example 3 | $Mo_{12}Bi_1Fe_3Ni_4Co_3Rb_{0.5}Mn_{0.2}Cr_{0.1}P_{0.05}Sb_1Si_8W_{0.3}$ | PMMA [0.40/2] |
| Comparative Example 4 | " | No addition |
| Comparative Example 12 | " | PMMA [100/2] |
| Example 4 | $Mo_{12}Bi_1Fe_{2.5}Ni_7Tl_{0.2}Sn_{0.5}Sb_{0.9}S_{0.2}$ | PMMA [0.80/4] |
| Comparative Example 5 | " | No addition |
| Comparative Example 13 | " | PMMA [20/4] |
| Example 5 | $Mo_{12}Bi_{0.5}Fe_{2.5}Ni_8K_{0.4}Sb_1Si_1Te_{0.3}$ | PMMA [2.0/5] |
| Comparative Example 6 | " | No addition |
| Comparative Example 14 | " | PMMA [50/5] |
| Example 6 | $Mo_{12}Bi_{0.7}Fe_3Ni_3Co_4K_{0.1}Cs_{0.5}Pb_{0.5}Sn_{0.5}Sb_{1.2}W_{0.3}$ | Polystyrene [2.0/3] |
| Comparative Example 7 | " | No addition |
| Comparative Example 15 | " | Polystyrene [50/3] |
| Example 7 | $Mo_{12}Bi_1Fe_3Ni_5Co_2Cs_{0.5}Mg_{0.5}Zn_{0.5}B_{0.3}Sb_1W_{0.5}$ | Polystyrene [5.0/3] |
| Comparative Example 8 | " | No addition |
| Comparative Example 16 | " | Polystyrene [100/3] |
| Example 8 | $Mo_{12}Bi_1Fe_{2.5}Ni_7Rb_{0.5}Mg_2$ | Polyisobutyl methacrylate [5.0/4] |
| Comparative Example 9 | " | No addition |
| Comparative Example 17 | " | Polyisobutyl methacrylate [100/4] |
| Example 9 | $Mo_{12}Bi_1Fe_3Ni_7Tl_{0.3}Zn_1Mn_{0.5}Sb_{1.5}Te_{0.3}W_{0.8}Ce_{0.2}$ | PMMA [2.03] + polystyrene [5.0/2] |
| Comparative Example 10 | " | No addition |
| Comparative Example 18 | " | PMMA [100/3] + polystyrene [50/2] |

| Reaction temperature (°C.) | Conversion of isobutylene (%) | Selectivity of methacrolein (%) | Selectivity of methacrylic acid (%) | per-pass yield of (methacrolein + methacrylic acid) (%) |
|---|---|---|---|---|
| 360 | 95.5 | 86.7 | 5.2 | 87.8 |

TABLE 1-continued

| | | | | |
|---|---|---|---|---|
| 360 | 95.0 | 85.8 | 5.0 | 86.3 |
| 360 | 94.8 | 85.6 | 4.8 | 85.7 |
| 360 | 95.3 | 88.9 | 4.9 | 89.4 |
| 360 | 94.8 | 88.0 | 4.6 | 87.8 |
| 360 | 94.5 | 87.7 | 4.4 | 87.0 |
| 355 | 91.3 | 87.3 | 4.5 | 83.8 |
| 355 | 90.1 | 87.1 | 4.2 | 82.3 |
| 355 | 90.5 | 86.6 | 4.0 | 82.0 |
| 355 | 92.1 | 88.0 | 5.1 | 85.7 |
| 355 | 91.0 | 86.6 | 4.9 | 83.3 |
| 355 | 90.6 | 86.2 | 4.7 | 82.4 |
| 365 | 96.0 | 86.8 | 5.5 | 88.6 |
| 365 | 95.6 | 85.9 | 5.1 | 87.0 |
| 365 | 95.1 | 85.9 | 4.7 | 86.2 |
| 365 | 96.8 | 88.7 | 3.8 | 89.5 |
| 365 | 96.2 | 87.5 | 3.8 | 87.8 |
| 365 | 96.1 | 87.5 | 3.6 | 87.5 |
| 380 | 63.2 | 73.6 | 4.6 | 49.4 |
| 380 | 61.5 | 71.1 | 4.3 | 46.4 |
| 380 | 61.0 | 70.6 | 4.2 | 45.6 |
| 370 | 98.0 | 85.3 | 4.5 | 88.0 |
| 370 | 97.8 | 84.1 | 3.9 | 86.1 |
| 370 | 97.5 | 83.5 | 4.0 | 85.3 |

As explained above, the catalysts prepared by the process of the present invention have a pore structure desirable for vapor phase catalytic oxidation reaction of isobutylene or tertiary butanol and have the advantageous effect to improve total selectivity of methacrolein and methacrylic acid.

What is claimed is:

1. A process for preparing a catalyst used for production of methacrolein and methacrylic acid by vapor phase catalytic oxidation of isobutylene or tertiary butanol which comprises adding an organic high-molecular weight compound selected from the group consisting of polymethyl methacrylate, polyisobutyl methacrylate and polystyrene, and having an average particle size of 0.01 μm to 10 μm to a catalyst component having the composition represented by the formula:

$Mo_aBi_bFe_cA_dX_eY_fZ_gO_h$ wherein Mo, Bi, Fe and O denote molybdenum, bismuth, iron and oxygen, respectively, A denotes at least one element selected from the group consisting of nickel and cobalt, X denotes at least one element selected from the group consisting of potassium, rubidium, cesium and thallium, Y denotes at least one element selected from the group consisting of magnesium, zinc, manganese, lead, tin and chromium, Z denotes at least one element selected from the group consisting of phosphorus, boron, antimony, silicon, sulfur, tellurium, tungsten and cerium, a, b, c, d, e, f, and g denote atomic ratios of respective elements, and when a is 12, b is 0.01–3, c is 0.5–4, d is 1–12, e is 0.01–2, f is 0–5 and g is 0–20, and h is the number of oxygen atoms necessary to satisfy valences of the above respective components to obtain a mixture, molding the resulting mixture to obtain a molded product and heat treating the molded product.

* * * * *